United States Patent
Wersland et al.

(10) Patent No.: US 11,571,331 B2
(45) Date of Patent: Feb. 7, 2023

(54) TEMPERATURE CONTROLLED AND VIBRATING THERAPEUTIC GARMENT

(71) Applicant: Therabody, Inc., Los Angeles, CA (US)

(72) Inventors: Jason Wersland, Los Angeles, CA (US); Benjamin Nazarian, Los Angeles, CA (US); Jaime Sanchez Solana, Los Angeles, CA (US); Eduardo Merino, Los Angeles, CA (US); Tim Roberts, Los Angeles, CA (US); Kevin Xie, Los Angeles, CA (US); Bill Webb, San Francisco, CA (US); Daniel S. Davidson, Seattle, WA (US); Corentin Guebels, Seattle, WA (US); Michael Prochaska, Seattle, WA (US); Luke David Springer, Seattle, WA (US); Alex Zhu, Xiamen (CN)

(73) Assignee: Therabody, Inc., Los Angeles, CA (US)

( * ) Notice: Subject to any disclaimer, the term of this patent is extended or adjusted under 35 U.S.C. 154(b) by 0 days.

(21) Appl. No.: 17/554,305

(22) Filed: Dec. 17, 2021

(65) Prior Publication Data

US 2022/0192868 A1    Jun. 23, 2022

Related U.S. Application Data (60) Provisional application No. 63/238,354, filed on Aug. 30, 2021, provisional application No. 63/167,533, (Continued)

(51) Int. Cl.
*A61F 7/02* (2006.01)
*A61H 23/00* (2006.01)
(Continued)

(52) U.S. Cl.
CPC ................ *A61F 7/02* (2013.01); *A61F 7/007* (2013.01); *A61H 23/00* (2013.01); *G05D 23/24* (2013.01);
(Continued)

(58) Field of Classification Search
CPC combination set(s) only.
See application file for complete search history.

(56) References Cited

U.S. PATENT DOCUMENTS

| 6,093,164 A | 7/2000 | Davis |
| 7,207,953 B1 | 4/2007 | Goicaj |

(Continued)

FOREIGN PATENT DOCUMENTS

| CN | 106691810 A | 5/2017 |
| KR | 200197414 Y1 | 11/2000 |
| WO | 2018064220 A1 | 4/2018 |

OTHER PUBLICATIONS

International Search Report and Written Opinion issued in PCT/US2021/064027.

*Primary Examiner* — Joseph A Stoklosa
*Assistant Examiner* — Adam J Avigan
(74) *Attorney, Agent, or Firm* — Sterne, Kessler, Goldstein & Fox P.L.L.C.

(57) ABSTRACT

A temperature controllable wrap assembly that includes a wrap portion configured to be worn around a user's body part, and at least a first temperature control module positioned on the wrap portion. The first temperature control module includes a housing, a controllable temperature element, a spreader member and at least a first finger spreader pivotably attached to the spreader member. The lower surface of the spreader member is positioned to contact the user's body part. The controllable temperature element is configured to transfer thermal energy to an upper surface of (Continued)

the spreader member, and the spreader member is configured to conduct thermal energy to the first finger spreader.

20 Claims, 9 Drawing Sheets

Related U.S. Application Data filed on Mar. 29, 2021, provisional application No. 63/126,954, filed on Dec. 17, 2020.

(51) Int. Cl.
*A61F 7/00* (2006.01)
*G05D 23/24* (2006.01)
*A61H 23/02* (2006.01)

(52) U.S. Cl.
CPC .......... *A61F 2007/0057* (2013.01); *A61F 2007/0075* (2013.01); *A61F 2007/0093* (2013.01); *A61F 2007/0228* (2013.01); *A61F 2007/0233* (2013.01); *A61H 23/0263* (2013.01); *A61H 2201/0214* (2013.01); *A61H 2201/165* (2013.01)

(56) References Cited

U.S. PATENT DOCUMENTS

| | | | |
|---|---|---|---|
| 8,764,688 B1 | 7/2014 | Nauman | |
| 9,017,273 B2 | 4/2015 | Burbank | |
| 9,125,442 B2 | 9/2015 | Brown | |
| 9,414,954 B2 | 8/2016 | Brown | |
| 9,549,870 B2 | 1/2017 | Shafieloo | |
| 9,901,510 B2 | 2/2018 | Smith | |
| 10,123,937 B2 | 11/2018 | Pisharodi | |
| 10,159,623 B2 | 12/2018 | Leftly | |
| 10,245,208 B2 | 4/2019 | MacGuinness | |
| 10,314,762 B1 | 6/2019 | Marton | |
| 10,406,024 B2 | 9/2019 | Evans | |
| 10,555,681 B2 | 2/2020 | Sun | |
| 10,632,040 B2 | 4/2020 | Muench | |
| 10,779,764 B2 | 9/2020 | Marlinski | |
| 2007/0255187 A1 | 11/2007 | Branch | |
| 2008/0188915 A1* | 8/2008 | Mills | A61F 7/007 607/112 |
| 2010/0249637 A1 | 9/2010 | Walter | |
| 2011/0000516 A1 | 1/2011 | Hershberger | |
| 2013/0085552 A1* | 4/2013 | Mandel | A61F 7/007 607/99 |
| 2014/0316311 A1 | 10/2014 | Nauman | |
| 2014/0350441 A1 | 11/2014 | Shafieloo | |
| 2014/0364778 A1 | 12/2014 | Leftly | |
| 2015/0174002 A1 | 6/2015 | Burbank | |
| 2015/0223975 A1* | 8/2015 | Anderson | A61F 7/10 607/104 |
| 2016/0058657 A1 | 3/2016 | Lal | |
| 2016/0089299 A1 | 3/2016 | Munoz | |
| 2016/0228325 A1 | 8/2016 | Kologrivov | |
| 2016/0331631 A1 | 11/2016 | Odi | |
| 2016/0346153 A1 | 12/2016 | Hodges, IV | |
| 2017/0119620 A1 | 5/2017 | Trapp | |
| 2017/0290736 A1 | 10/2017 | Idris | |
| 2018/0042810 A1 | 2/2018 | Nguyen | |
| 2018/0065517 A1 | 3/2018 | Kuhley | |
| 2018/0140506 A1 | 5/2018 | Smith | |
| 2018/0228689 A1 | 8/2018 | Lach | |
| 2018/0303704 A1 | 10/2018 | Idris | |
| 2019/0070068 A1 | 3/2019 | Pisharodi | |
| 2019/0151190 A1 | 5/2019 | Burbank | |
| 2019/0183724 A1 | 6/2019 | Sifferlin | |
| 2019/0350752 A1* | 11/2019 | Aguiar | A61F 7/02 |
| 2020/0061316 A1 | 2/2020 | Inoue | |
| 2020/0078261 A1 | 3/2020 | Duvall | |
| 2020/0230021 A1 | 7/2020 | Pisharodi | |
| 2020/0368061 A1 | 11/2020 | Levinson | |

\* cited by examiner

TEMPERATURE CONTROLLED AND VIBRATING THERAPEUTIC GARMENT

CROSS-REFERENCE TO RELATED APPLICATIONS

This application claims the benefit of U.S. Provisional Application No. 63/238,354, filed Aug. 30, 2021, U.S. Provisional Application No. 63/167,533, filed Mar. 29, 2021 and U.S. Provisional Patent Application No. 63/126,954, filed Dec. 17, 2020, the entireties of which are incorporated by reference herein.

FIELD OF THE INVENTION

The present invention relates to a therapeutic garment, strap or wrap, and more particularly to a therapeutic garment, strap or wrap that includes temperature control and vibration.

BACKGROUND OF THE INVENTION

One issue with wraps, garments and straps used for cooling or icing body parts that have a curvature to them is maintaining contact with a user's skin. The undulations or curvature often cause issues. Accordingly, a need exists for a wrap that provide heat transfer to the user's body part while maintaining good contact with the user's skin.

The background description disclosed anywhere in this patent application includes information that may be useful in understanding the present invention. It is not an admission that any of the information provided herein is prior art or relevant to the presently claimed invention, or that any publication specifically or implicitly referenced is prior art.

SUMMARY OF THE PREFERRED EMBODIMENTS

In accordance with a first aspect of the present invention there is provided a temperature controllable wrap assembly that includes a wrap portion configured to be worn around a user's body part, and at least a first temperature control module positioned on the wrap portion. The first temperature control module includes a housing, a controllable temperature element, a spreader member and at least a first finger spreader pivotably attached to the spreader member. A lower surface of the spreader member is positioned to contact the user's body part. The controllable temperature element is configured to transfer thermal energy to an upper surface of the spreader member and the spreader member is configured to conduct thermal energy to the first finger spreader. Preferably, the lower surface of the spreader member is curved.

In a preferred embodiment, the first finger spreader is pivotable between a first position and a second position. In the second position a distal end of the first finger spreader is positioned below the lower surface of the spreader member. Preferably, the spreader member includes a knuckle portion, the first finger spreader includes a pin portion that is received in the knuckle portion and the pin portion is rotatable within the knuckle portion. In a preferred embodiment, the temperature controllable wrap assembly includes a main control module in electrical communication with the first temperature control module (electrical communication can be power, data or both). The main control module includes a removable battery, an upper battery opening defined in an upper surface and a lower battery opening defined in a lower surface. The battery includes a lower surface that is exposed through the lower battery opening and an upper surface that is exposed through the upper battery opening. The battery is removable by pushing on the lower surface of the battery and removing the battery through the upper surface (or vice versa). Preferably, the battery includes a magnet for holding the battery within the main control module. The main control module includes a battery attracted to the magnet in the battery.

In a preferred embodiment, the temperature controllable wrap assembly includes a second temperature control module positioned on the wrap portion that includes a housing, a controllable temperature element, a spreader member and at least a first finger spreader pivotably attached to the spreader member. A lower surface of the spreader member is positioned to contact the user's body part. The controllable temperature element is configured to transfer thermal energy to an upper surface of the spreader member. The spreader member is configured to conduct thermal energy to the first finger spreader. The first finger spreader of the first temperature control module extends outwardly in a first direction and the first finger spreader of the second temperature control module extends outwardly in a second direction. The first direction is generally opposite of the second direction.

In a preferred embodiment, the temperature controllable wrap assembly includes first and second vibration devices embedded in the wrap portion. The wrap portion comprises a center axis that extends between the first and second temperature control modules (and through the central opening). The first temperature control module is positioned between the first vibration device and the center axis and the second temperature control module is positioned between the second vibration device and the center axis.

In a preferred embodiment, a thermistor is embedded in the spreader member. The thermistor is received in a thermistor opening defined in the upper surface of the spreader member, a groove is defined in the upper surface of the spreader member, and a wire extends from the thermistor and through the groove.

In accordance with another aspect of the present invention there is provided a temperature control module that includes a housing, a controllable temperature element having first and second opposing surfaces, a heat sink positioned in the housing and in contact with the first surface of the controllable temperature element, a fan positioned in the housing and configured to direct heat away from the heat sink, a spreader member and at least a first finger spreader pivotably attached to the spreader member. The controllable temperature element is configured to transfer thermal energy to an upper surface of the spreader member and the spreader member is configured to conduct thermal energy to the first finger spreader. In a preferred embodiment, the temperature control module includes a second finger spreader. The first and second finger spreaders are pivotable with respect to the housing independently from one another. The spreader member includes first and second opposing edges and third and fourth opposing edges. The first finger spreader extends outwardly past the first edge and the second finger spreader extends outwardly past the third edge such that the first and second finger spreaders (or a longitudinally extending axis thereof) are perpendicular to one another.

Preferably, the spreader member includes a knuckle portion. The first finger spreader includes a pin portion that is received in the knuckle portion, and the pin portion is rotatable within the knuckle portion. Preferably a thermistor is embedded in the spreader member. The thermistor is received in a thermistor opening defined in the upper surface of the spreader member, a groove is defined in the upper surface of the spreader member, and a wire extends from the thermistor and through the groove.

Described herein is a garment that includes temperature and vibration therapy integrated therein. In a preferred embodiment, the garment or wrap portion is stretchable and compresses against the wearer's skin. For example, see U.S. Pat. Nos. 9,125,442 and 9,414,954, the entireties of which are incorporated by reference herein. Any garment, wrap, strap or portion of a garment is within the scope of the present invention. For example, the wrap assembly can be used on a limb or can be a shirt (long sleeve or short sleeve), pants, shorts, tank top, bra, sleeve, sock(s) or the like. In another embodiment, the garment can be a compression wrap or sleeve that surrounds a specific body part (and can include straps for securing in place), such as a knee, ankle, shoulder or the like. The compression wrap can also include heating or cooling capability. For example, see U.S. Pat. No. 10,406,024 (the '024 patent), the entirety of which is incorporated by reference herein.

In a preferred embodiment, the inventive wrap assembly or garment provides vibration therapy treatment to the wearer. In a preferred embodiment, the vibration devices, motors or unit cells used in the garment generate a vibration with an amplitude smaller than 20 mm (e.g., 0.2 mm to 20 mm). It will be appreciated that the vibration can provide blood flow and oxygen increases in the wearer's body. These vibration devices are small enough that they can be integrated into wearables, fabrics, garments and pieces of clothing. As a result, the garments can be used for not only pre-exercise and post-exercise treatments, but also can be used during exercise. It will be appreciated that this type of motor is not a limitation on the present invention. Any type of motor that provides the desired vibration or amplitude is within the scope of the present invention. For example, the motor can include an electromagnet coil through which a shaft extends and where the shaft reciprocates (is pushed and pulled) as a result of the magnetic field produced by the coil. The shaft can include some type of member or portion thereon that provides the vibration or percussion on the wearer's skin.

The elastic, compressive fabric or wrap portion can be made of, e.g., nylon, spandex, neoprene or other flexible fabric or material. The garment or wrap portion can include multiple fabric layers, for example, inner and outer layers to accommodate or house the components (e.g., the actuator and sensor layer(s)) and provide a space or pathways for the electronics and circuit boards. The fabric may also include breathable areas as well as sealed sections to waterproof cabling and electronics.

In a preferred embodiment, the wrap assembly includes wireless communication (e.g., Bluetooth) so that it can communicate with a software application on a mobile device, such as a phone to provide a "smart" garment system. The wireless communication device can be housed on a PCB that is also in electrical and/or data communication with the vibration devices, temperature control modules, main control module or the like.

In another preferred embodiment, the garment assembly includes temperature control or modulation. In particular, the garment assembly can include temperature control modules that may be permanent or removable.

The wearable device or garment assembly can include temperature modulation and application, for example, via temperature control modules positioned thereon or integrated therein. The garment assembly can include both vibration and heat/cold or can include one or the other. In a preferred embodiment, the wrap portion includes a magnet positioned thereon or therein. At at least some locations on the garment portion, temperature control modules can be secured to the magnets. Temperature control modules can be disposed throughout the garment assembly. In a preferred embodiment, there is no garment or fabric layer between the temperature control module and the user's skin. Instead, the bottom layer or surface of the temperature control module or some other heat conductive portion or material contacts the user's skin.

In a preferred embodiment, the temperature control module includes a fan, a heat sink and a peltier module or device that are contained within the module housing. In this embodiment, the temperature control module includes a magnet on the bottom thereof that can be magnetically connected or secured to a magnet on or in the fabric portion or garment portion of the garment assembly. A frame (e.g., plastic frame) can be embedded in or attached to the garment portion for helping with connection of the temperature control module.

In a preferred embodiment, the magnet to magnet system secures the temperature control module to the wrap or garment portion and transfers or conducts the heat or cold from the module to the user's skin as the magnets are preferably made of a heat and/or cold conductive material. In an embodiment, the wrap assembly can include a flexible heat or cold conductive members, such as a band, patch or the like (e.g., made of copper or aluminum) to help transfer heat or cold to increase the effective area of the heat/cold treatment. The heat conductive members are preferably in contact with or connected to the magnet so that the heat or cold is conducted from the magnet and through the heat conductive member.

In an embodiment with a number of connecting magnets in different locations, the user is provided with a plurality of options for where to position one or more temperature control modules. For example, if the user has a right shoulder issue they are treating, they may only place one or more temperature control modules in that location. At a later time they can use the same shirt to treat an abdominal issue. The vibration devices may be embedded in the garment portion (e.g., between inner and outer fabric layers) and can be arranged around the magnets such that temperature control modules can be connected to the magnet above and below the knee cap. This is just an example and any pattern or number of vibration devices and temperature control modules can be utilized. It will be appreciated that any configuration of vibration devices is within the scope of the present invention. The vibration devices can be configured to treat certain issues and can be placed in patterns around the sleeve or wrap, such as a triangle, star, circle, spiral, other pattern, etc. and can increase blood flow and provide therapeutic benefit as desired.

In a preferred embodiment, the garment assembly includes a plurality of magnets that may be overlapping or a single magnet with a plurality of locations where the magnet on the temperature control modules can be placed in order to allow the temperature control modules to be movable or positionable within the same general area. This allows the user to move the module to the exact location of the issue. It also allows a single garment size to be usable by different uses (because no two bodies are exactly the same). In another embodiment, the majority of or all of the garment can be magnetized, thus allowing the module to attach anywhere.

In a preferred embodiment, the invention includes a smart vibration system. It will be appreciated by those of ordinary skill in the art that at a certain frequency (depending on the mass attached to the system), vibrations can make a user's body resonate and therefore increase the amplitude of the perceived vibration. To take advantage of this resonant frequency principle (which is different from person to person and from body part to body part), the present invention may include a closed loop system with sensors that scan through the different speeds of the vibration devices or motors until the resonant frequency is found. This may be accomplished by adding accelerometers near the motor locations that can measure the actual vibration it is being generated when the motor is attached to the body part. In an exemplary embodiment, strain gages that can measure displacement of the garment are included in the location of the motor.

In a preferred embodiment, the garment assembly is washable and includes at least some components that are embedded in, attached to, etc. permanently in the garment (e.g., waterproof enclosed motors, cabling, etc) and other components that are removable (battery pack, PCB). The permanent components are preferably sealed in the garment (e.g., between garment layers and the user can wash the garment after removing the power unit system (battery pack, PCB, etc.).

In another preferred embodiment, the garment assembly can be a wrap or strap garment assembly that includes a heating/cooling system and localized vibration. In a preferred embodiment, the garment assembly is incorporated in a compression wrap. One or more of the layers of the device can include vibration capability. The temperature control modules may or may not contain an integrated battery (i.e., within the module). The modules can be removed from the strap device and placed in different cavities in the strap assembly depending on the desired treatment.

The temperature control modules may be different sizes depending on the muscle group or the surface area desired be treated. The device (or separate devices) may also include different sized and shaped straps to accommodate different body parts.

The wrap assembly may be embodied in a wrist and/or knee strap assembly. In a preferred embodiment, the wrap portion may include positions or cavities defined therein that are each configured to receive a temperature control module. The main controller can be electrically connected to and in data communication with the temperature control modules so that the modules are powered and can be controlled by the controller. The wiring can be embedded in the main body portion and plugs or jacks can be used for attaching and detaching the electrical connections. The wiring can also be external. Wireless connectivity between any and/or all components can also be included. In another embodiment, a battery can be located in the module, thus making each module independent and interchangeable such that it can be simply placed in the cavity or a strap garment assembly or secured via a magnet or other attachment mechanism to a "wearable" garment assembly.

In a preferred embodiment, the module housing includes a groove therearound that receives a portion of the wrap portion so that it can be positioned in the cavity (or module seat). It will be appreciated that the wrap portion is made of a material that is pliable and flexible enough to allow the modules to be inserted into the cavities and removed therefrom (e.g., pressed into place and removed therefrom). In embodiments with larger and smaller modules, the one or more larger modules are the main heat or cold provider (to the user). The heat is preferably conducted outwardly from the larger module. The smaller modules can be used to provide extra heat or cold where it is difficult to conduct the heat from the larger module. In a preferred embodiment, the main body portion and/or straps include heat conductive material therein or thereon.

In an embodiment, the wrap assembly may include different sized modules, such as one larger module and several smaller modules. Some or all of the temperature control modules may also include vibration devices or motors therein (e.g., inside the housing). In another embodiment, one or more vibrating devices can be placed on or in the heat sink. Vibration devices can also be included embedded in the main body portion or strap portions. It will be appreciated that any and all of the embodiments discussed or disclosed herein and any of the components or concepts included in the embodiments are all completely interchangeable, swappable and usable together. It will be appreciated that strap assemblies or wrap portions can be configured to fit any body part or multiple body parts, e.g., shoulder, back, knee, elbow, wrist, neck, ankle, etc.

in a preferred embodiment, the temperature control module May include a concave module structure or bottom surface so that it can adapt to the contour of different portions of the body, such as the thigh, calf, Shin, etc. In a preferred embodiment, the temperature control module also includes a fan bracket and a peltier housing that includes an upper housing portion that houses the peltier device and a lower housing portion that houses the vibration device and a PCB. Preferably, the module housing includes a lower portion that includes the concave surface on a bottom thereof. The lower portion also includes a conductive member that conducts heat or cold from the peltier device to the concave bottom surface. The upper and lower housing portions of the peltier housing define a vibration device recess. All temperature control modules herein include vents or openings in the module housing to allow heat to be dissipated therefrom. It will be appreciated that the straps can be include velcro or the like for securement.

In a preferred embodiment, the main control module or assembly includes a plurality of buttons and/or switches thereon for controlling the temperature control modules and/or vibration devices. For example, the buttons can control turning the device on and off, cooling and heating, time or duration, changing modes, controlling the vibration devices and turning them on and/or off for various body parts. LED lights can also be included as charging or time indicators. Some of the features are controlled by multiple pushes of the associated button. In an exemplary embodiment, the buttons may work as follows. Pushing the mode button may cycle through the following vibration patterns—constant, wave, regular, wave, off. The cold button—one press for 5° C. control, two presses for 10° C. control, three presses for unlimited control and four presses to turn off. The hot button—one press for 38° C. control, two presses for 40° C. control, three presses for 42° and four presses to turn off. The time button—power on sets the time to 15 minutes, one press sets to 30 minutes, two presses sets to 60 minutes, third press for unlimited time.

One of the advantages of the present invention is the ability to provide flexibility so that the modules can be used on, for example, strap devices and garment or wearable devices. Mounting the modules on strap devices provides high performance and efficacy. The strap allows for multiple modules to work together and treat a wide area. Mounting the modules on a wearable device (e.g., shirt, pants, shorts, etc.) provides the user with the a vibration garment and the flexibility of adding temperature control modules when desired.

It will be appreciated that the wrap assembly in a nutshell is a battery powered wearable that can replace ice packs and is shaped to treat body parts such as the shoulder and upper back. The assembly can also be used for heat therapy and may have several vibration motors embedded in the strap or garment to boost blood flow and recovery. In a preferred embodiment, the shoulder strap assembly includes a removable battery, at least three (and possible more) temperature control modules, eight to twelve modules (can include more or less) vibration motors in the garment or strap. Preferably, the motors are divided into groups of three and the speed or on and off of the groups can be controlled independently. Preferably, the device also includes Bluetooth connectivity that allows it to be connected to an app on a mobile device. Exemplary use cases for athletes and non-athletes include post shoulder surgery treatment, post work-out recovery, and users with chronic shoulder, neck and upper back pain.

It will be appreciated that the body parts that the strap assemblies may be used on include curved surfaces. In a preferred embodiment, the temperature control module includes extension members or finger spreaders that essentially increase the footprint of the cooling/heating modules and allow the invention to distribute the desired temperature around curved areas in the body (e.g., calf, thigh, shoulder, trapezoid). In an exemplary embodiment, the finger spreaders allow treatment area to extend around a curved surface.

In a preferred embodiment, the temperature control module includes modular extension legs, extension members or spreaders made of, e.g., stacks of thin copper. The spreaders can be divided into smaller fingers to add flexibility in the perpendicular direction and help adapting to the body. The spreaders can be attached to the main plate under the primary spreader by different methods, such as bolted (or other threaded receiver), riveted, hinged, welded, etc.

Vibration motors can be included in the strap, garment portion, within the housing or on the spreaders. The spreaders, spreader members, finger spreaders, legs or extension members can be made of aluminum or another metal and the pivot points or the like of the spreaders can be made of copper or other metal.

In a preferred embodiment, the spreaders 42 can be enclosed or sewn into the garment portion. The fabric or strap is preferably on top of the spreader, thereby allowing the bottom surface of the spreader to touch the skin of the user. In this embodiment, when the strap or garment portion is wrapped around the body part (e.g., leg), the spreaders 94 will be moved or pivoted by the fabric to help the spreaders move closer to or against the leg. The user can also push the spreaders through the fabric to help the spreader to the desired position.

In a preferred embodiment, the spreader member and/or finger spreaders can include a plurality of metallic layers. In such an embodiment, thin copper layers (e.g., die cut layers) are stacked on one another and form the separate primary spreader member and extension legs or finger spreaders. The extension legs can be pivotable with respect to the primary spreader or they may not be. Therefore, by creating the thin layers, the desired shape (depending on the body part targeted) can be created. The stack of layers can include layers of aluminum or thicker copper above and below in the areas were rigidity needs to be increased. Also, the copper layers can be formed in different shapes to adapt exactly to the geometry of the muscle(s) to be treated.

Any type of attachment system that can be used to secure the garment assembly to the user's leg or other body part is within the scope of the present invention. The attachment system may include a magnetic securement and adjustment system therein. The attachment system May include a mechanical latch or securement system and magnets for aligning the components to make connection easier. For example, a Fidlock magnetic buckle or system can be used.

In a preferred embodiment, the wrap assembly includes one or more pillow or cushion members on the inside of the wrap portion, which provide comfort for the user and may also be removable so that they can be washed or replaced. The cushion members may include magnets or other attachment mechanism (velcro, snaps, buttons, etc.) so that the cushion members can be secured or removably attached to the wrap portion. Upper and lower or first and second cushion portions can be included for the upper and lower portions. The cushion members provide a layer generally parallel to the thermal spreader surface that improves comfort and may be a layer that is sacrificed or replaced due to the buildup of sweat and moisture over time. Any soft material is within the scope of the invention. In a preferred embodiment, the cushion member includes a memory foam layer wrapped in a fabric enclosure. The magnets may be embedded in the memory foam or between layers (and a complementary magnet is included in the wrap portion). The thickness is selected to provide comfort while allowing the vibration motors to contact the user's skin.

The wrap assembly may include a mounting skirt and/or mounting member for mounting or otherwise attaching the temperature control modules and/or main control module to the wrap portion (e.g., by sewing). A donut or ring member may be positioned around the knee or central opening and helps align the wrap assembly on the user's knee cap when worn. The ring member is preferably semi-rigid to rigid and allows the knee cap of the user to at least partially extend therethrough to help support the wrap assembly on the user's leg and to help prevent the strap from sliding down the user's leg. Preferably the ring member is made of a plastic material so that it is rigid for support, but somewhat flexible so it can move and bend when the user bends their knee. The wrap portion preferably includes inner and outer layers so that some of the components (e.g., wiring, the donut for the central opening, etc.) can be sandwiched therebetween.

It will be appreciated that any type of system for holding the temperature control modules in place on a body part is within the scope of the present invention. Any type of straps, clamps, buckles and the like or combination thereof is within the scope of the present invention. Furthermore, the wrap portion or fabric portion of the assembly can be modified or changed to make the product smaller, streamlined or generally of a lighter weight. In a preferred embodiment, any portion or all of the wrap assembly/fabric portion can include, be comprised of, include a layer of or use a far infrared or FIR fabric.

BRIEF DESCRIPTION OF THE DRAWINGS

The invention may be more readily understood by referring to the accompanying drawings in which.

Like numerals refer to like parts throughout the several views of the drawings.

DETAILED DESCRIPTION OF THE PREFERRED EMBODIMENTS

The following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be, but not necessarily are references to the same embodiment; and, such references mean at least one of the embodiments. If a component is not shown in a drawing then this provides support for a negative limitation in the claims stating that that component is "not" present. However, the above statement is not limiting and in another embodiment, the missing component can be included in a claimed embodiment.

Reference in this specification to "one embodiment," "an embodiment," "a preferred embodiment" or any other phrase mentioning the word "embodiment" means that a particular feature, structure, or characteristic described in connection with the embodiment is included in at least one embodiment of the-disclosure and also means that any particular feature, structure, or characteristic described in connection with one embodiment can be included in any embodiment or can be omitted or excluded from any embodiment. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others and may be omitted from any embodiment. Furthermore, any particular feature, structure, or characteristic described herein may be optional. Similarly, various requirements are described which may be requirements for some embodiments but not other embodiments. Where appropriate any of the features discussed herein in relation to one aspect or embodiment of the invention may be applied to another aspect or embodiment of the invention. Similarly, where appropriate any of the features discussed herein in relation to one aspect or embodiment of the invention may be optional with respect to and/or omitted from that aspect or embodiment of the invention or any other aspect or embodiment of the invention discussed or disclosed herein.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks: The use of highlighting has no influence on the scope and meaning of a term; the scope and meaning of a term is the same, in the same context, whether or not it is highlighted.

It will be appreciated that the same thing can be said in more than one way. Consequently, alternative language and synonyms may be used for any one or more of the terms discussed herein. No special significance is to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

It will be appreciated that terms such as "front," "back," "top," "bottom," "side," "short," "long," "up," "down," "aft," "forward," "inboard," "outboard" and "below" used herein are merely for ease of description and refer to the orientation of the components as shown in the figures. It should be understood that any orientation of the components described herein is within the scope of the present invention.

Described herein and shown in FIGS. 1-10 is a temperature controllable wrap assembly 10 that preferably includes temperature control and vibration therapy integrated therein. FIGS. 1-10 show the garment assembly embodied in a closeable sleeve or wrap that is configured to be used on a wearer's knee. However, it will be appreciated that this is not a limitation on the present invention and the wrap assembly 10 can be any type of wearable garment, wrap or strap that includes the temperature control modules disclosed herein.

Figure 1:
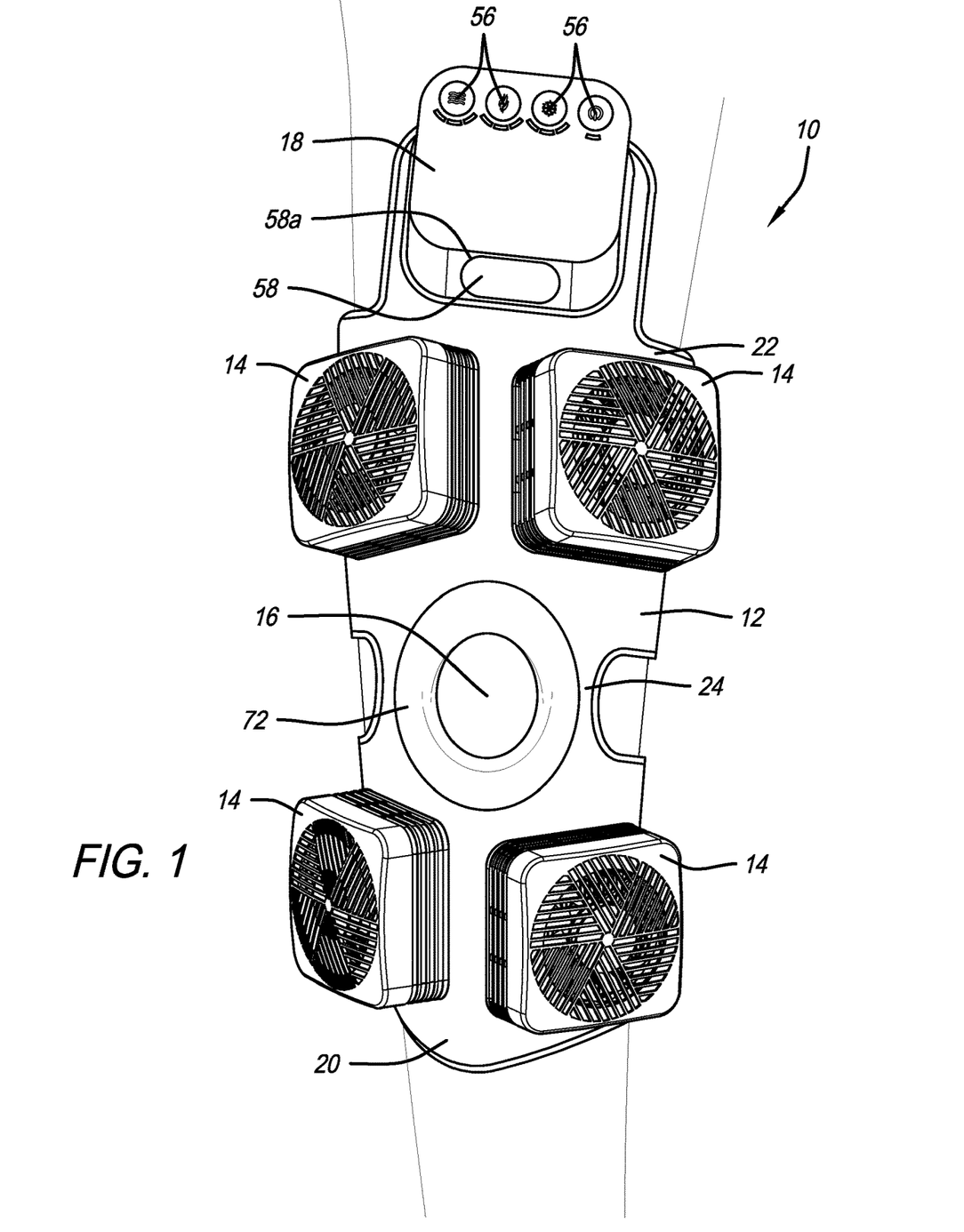
FIG. 1 is a perspective view of a temperature controllable wrap assembly secured on a user's leg in accordance with a preferred embodiment of the present invention attached thereto.
Figure 2:
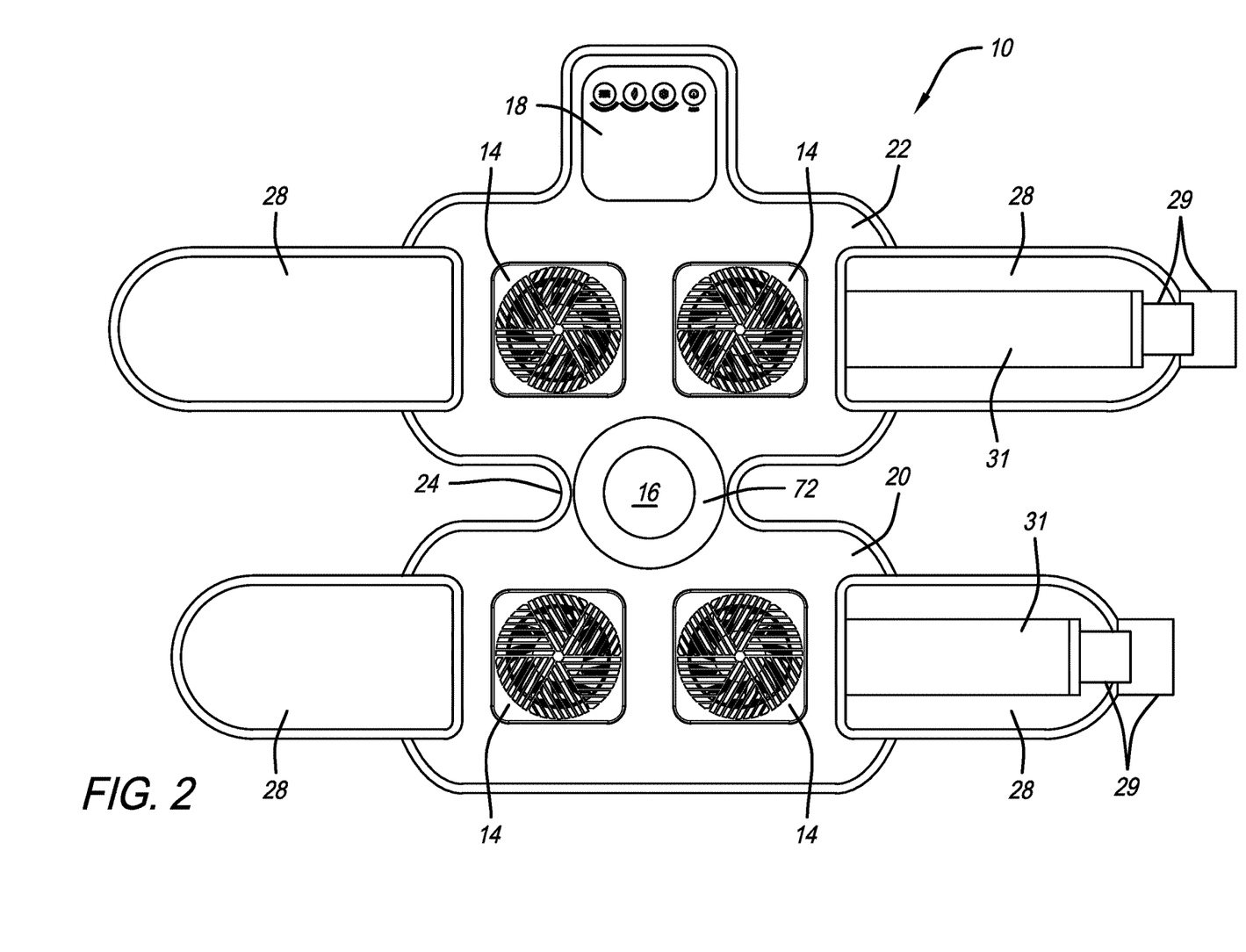
FIG. 2 is a front elevational view of the temperature controllable wrap assembly of FIG. 1.
Figure 3:
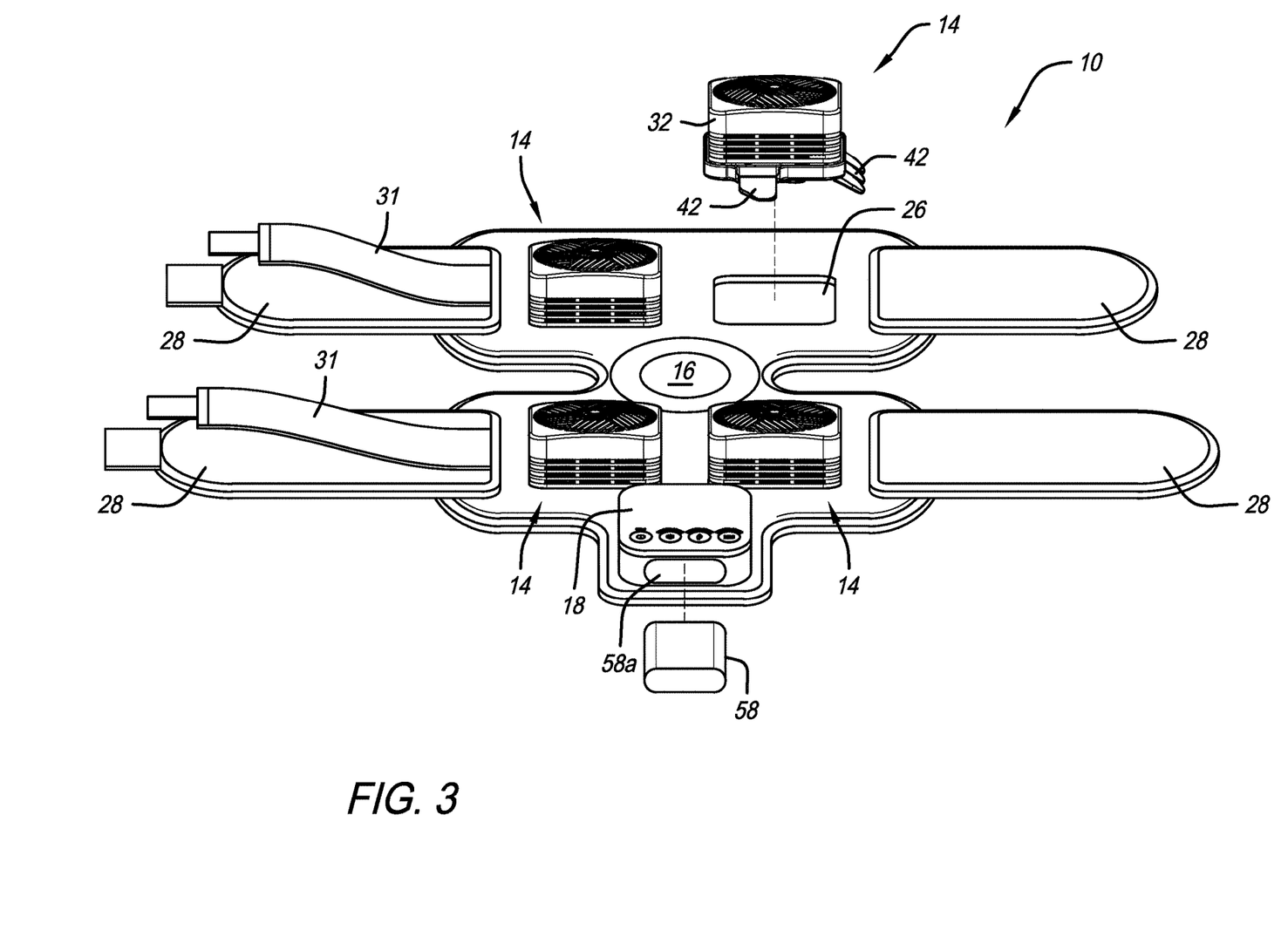
FIG. 3 is a front perspective view of the temperature controllable wrap assembly of FIG. 1 in the open position.

As shown in FIG. 1, in a preferred embodiment, the temperature controllable wrap assembly 10 includes a garment or wrap portion 12 configured to be worn around a user's leg, a plurality of temperature control modules 14 positioned on or extending through the wrap portion 12, a central opening 16, and a main control module 18. As shown in FIGS. 2 and 3, in a preferred embodiment, the wrap portion 12 includes a lower portion 20, an upper portion 22 and a knee portion 24 extending between the lower portion 20 and the upper portion 22. Preferably, the central opening 16 is at least partially defined in or through the knee portion 24.

In a preferred embodiment, the temperature control modules 14 are mounted in retention openings 26 defined in the wrap portion 12 (which may include one or more layers). As shown in FIG. 2, in a preferred embodiment, two temperature control modules 14 and the main control module 18 are positioned on the upper portion 22 and two temperature control modules 14 are positioned on the lower portion 20. In a preferred embodiment, strap portions 28 extend outwardly from the upper and lower leg portions. Preferably, one of the strap portions 28 includes a handle 29 for pulling the strap portion to provide the desired amount of tension and securing to the strap portion on the other side. Preferably, the strap portions 28 include hook and loop material 30 (Velcro) thereon so that the temperature controllable wrap assembly 10 can be secured around the user's leg. As shown in FIG. 2, the wrap portion 12 can also include secondary straps 31 that provide the ability to further tighten the straps on one side to the Velcro strap on the other side. any arrangement of hook material on one strap and loop material on another strap is within the scope of the present invention to allow the strap portions 28 and secondary straps 31 to work is within the scope of the present invention. In another embodiment, the strap portions can be omitted and the wrap portion can be a closed sleeve that is stretchable to fit over the user's leg. It will be appreciated that any type of system for holding the temperature control modules in place on a body part is within the scope of the present invention. Any type of straps, clamps, buckles and the like or combination thereof is within the scope of the present invention.

Figure 4:
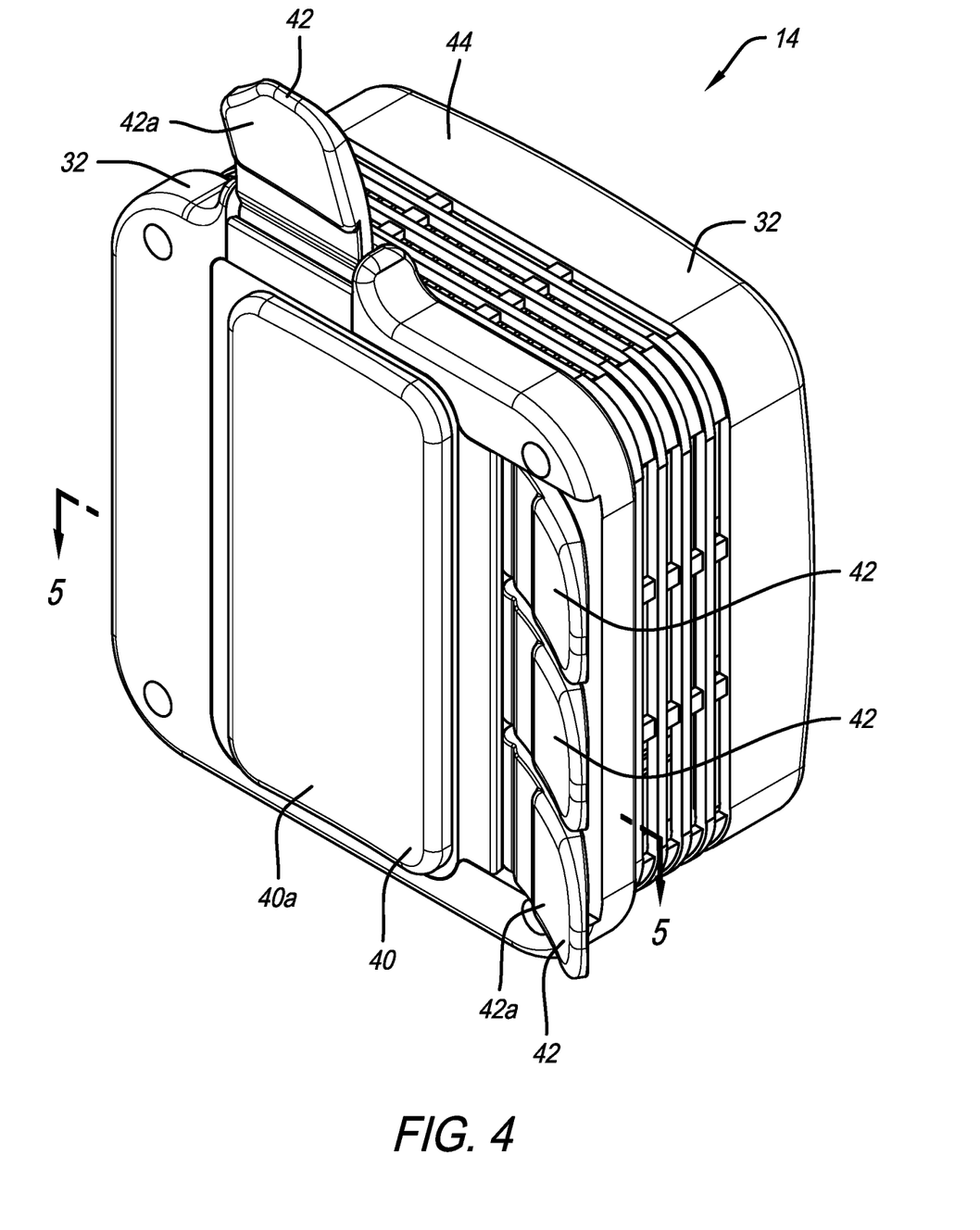
FIG. 4 is a perspective view of a temperature control module in accordance with a preferred embodiment of the present invention.
Figure 5:
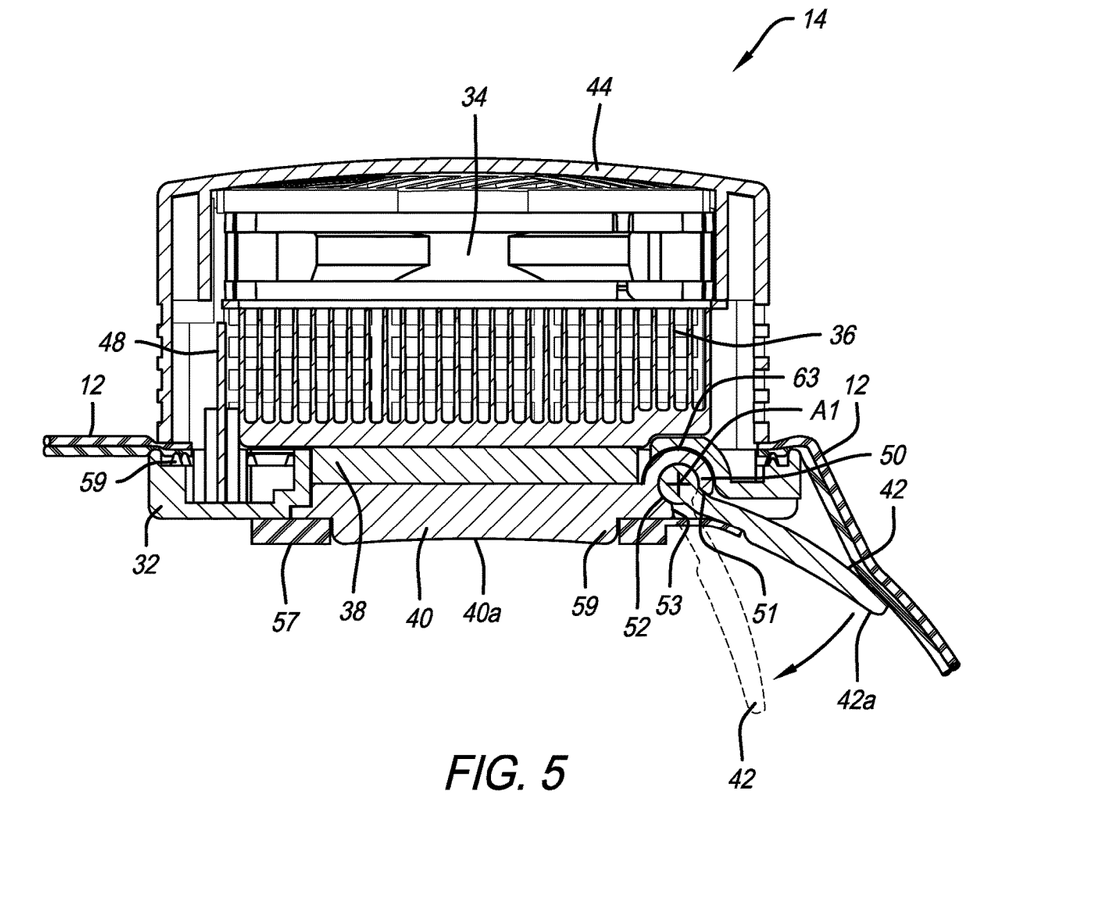
FIG. 5 is a cross-sectional view of the temperature control module.
Figure 6:
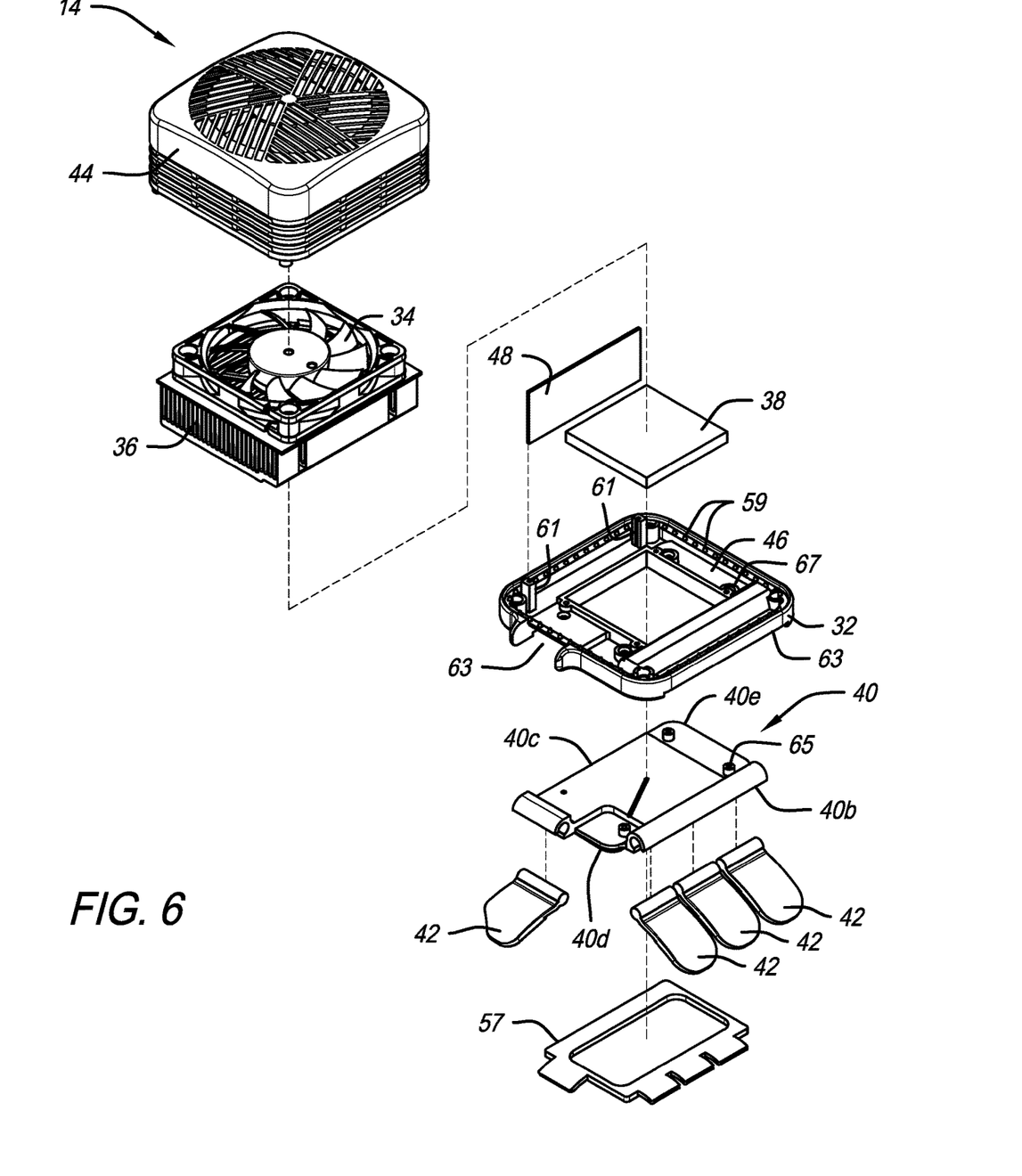
FIG. 6 is a an exploded perspective view of the temperature control module.

FIGS. 4-6 show a temperature control module 14. In a preferred embodiment, the temperature control module 14 includes a housing 32, a fan 34, a heat sink 36, a thermoelectric cooler, peltier device or controllable temperature element 38, a spreader plate or member 40 and a plurality of finger spreaders 42 that are pivotably attached to the spreader member 40. In a preferred embodiment, the housing 32 includes an upper portion 44 and a lower portion 46. In use, the lower surface 40a of the spreader member 40 and the inner or lower surface 42a are positioned to contact and transfer thermal energy (hot or cold) to the user's body part. As discussed above and herein, the lower surface of the controllable temperature element 38 is configured to transfer thermal energy to the upper surface of the spreader member 40 and heat sink 36 is configured to pull heat from the upper surface of the controllable temperature element 38. The fan 34 helps dissipate heat from the heat sink 36 and other components. In use, the primary spreader member 40 is cooled or heated by the controllable temperature element 38 and the heat or cold is conducted from the primary spreader 40 to the finger spreaders 42. In a preferred embodiment, the temperature control module 14 also includes a PCB 48 for electrical and data communication (with the main control module 18 or other controller) and controlling the module.

In a preferred embodiment, the spreader member 40 is configured to conduct thermal energy to the finger spreaders 42. The spreader member 40 includes first and second opposing edges 40b and 40c and third and fourth opposing edges 40d and 40e. In a preferred embodiment, finger spreaders 42 extend from and/or past a plurality of the outer edges of the spreader member. For example, as shown in FIG. 6, three finger spreaders 42 extend from the first edge 40b and one finger spreader extends from the third edge 40d. In another embodiment, one or more finger spreaders can extend from all or three edges.

Any type of pivotable connection between the finger spreaders and the spreader member is within the scope of the present invention. In a preferred embodiment, as shown in FIGS. 4 and 5, the finger spreaders 42 are hingedly attached to the spreader member 40. To provide the hinged connection, the spreader member 40 includes one or more knuckle portions 50 and the finger spreaders 42 include a pin portion 52 that is received in the knuckle portion 50. The contact portion 54 of the finger spreader 42 extends outside of knuckle portion 50 and the pin portion 52 is rotatable within the knuckle portion 50. FIG. 5 shows the finger spreader 42 in a first position in solid lines and a second position in dashed lines. In a preferred embodiment, in at least the second position, a distal end 42a of the finger spreader(s) 42 is positioned below the lower surface 40a of the spreader member 40.

Figure 9:
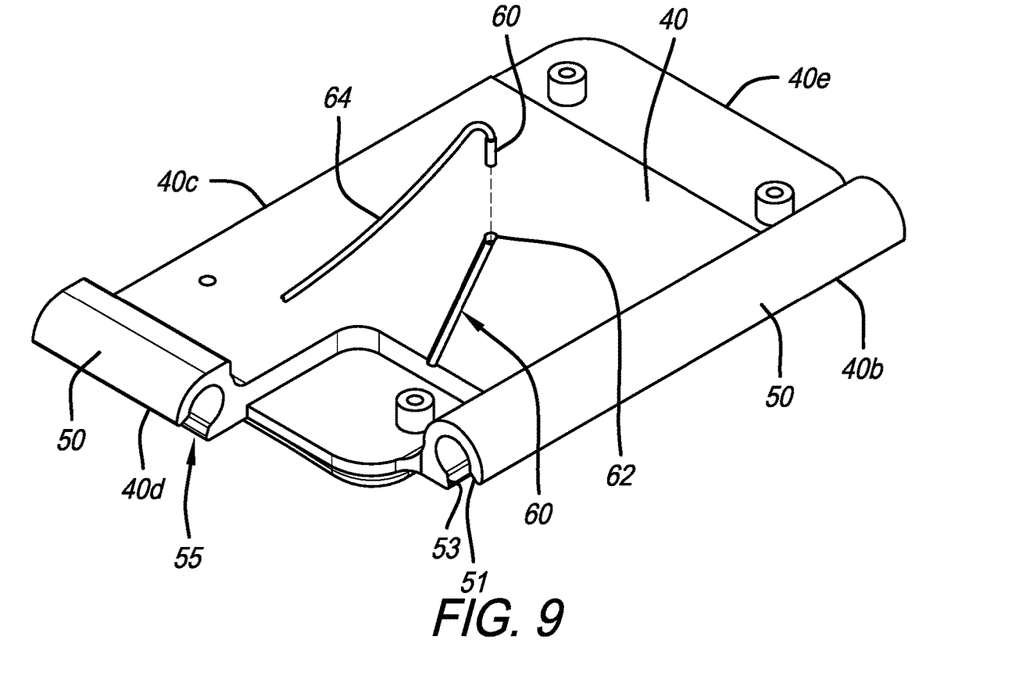
FIG. 9 is a perspective view of a spreader member with a thermistor exploded therefrom.

In a preferred embodiment, the knuckle portion 50 includes upper and lower stop members 51 and 53 that include a pivot space 55 therebetween (see FIG. 9). The finger spreaders 42 are pivotable within the pivot space 55 and between the upper and lower stop members 51 and 53. The upper and lower stop members 51 and 53 define the upper and lower limits of the pivot angle of the finger spreaders. FIG. 5 shows the finger spreader 42 in the first position in solid lines and with the upper surface against the upper stop member 51 and in the second position in dashed lines with the lower surface against the lower stop member 53.

Figure 7:
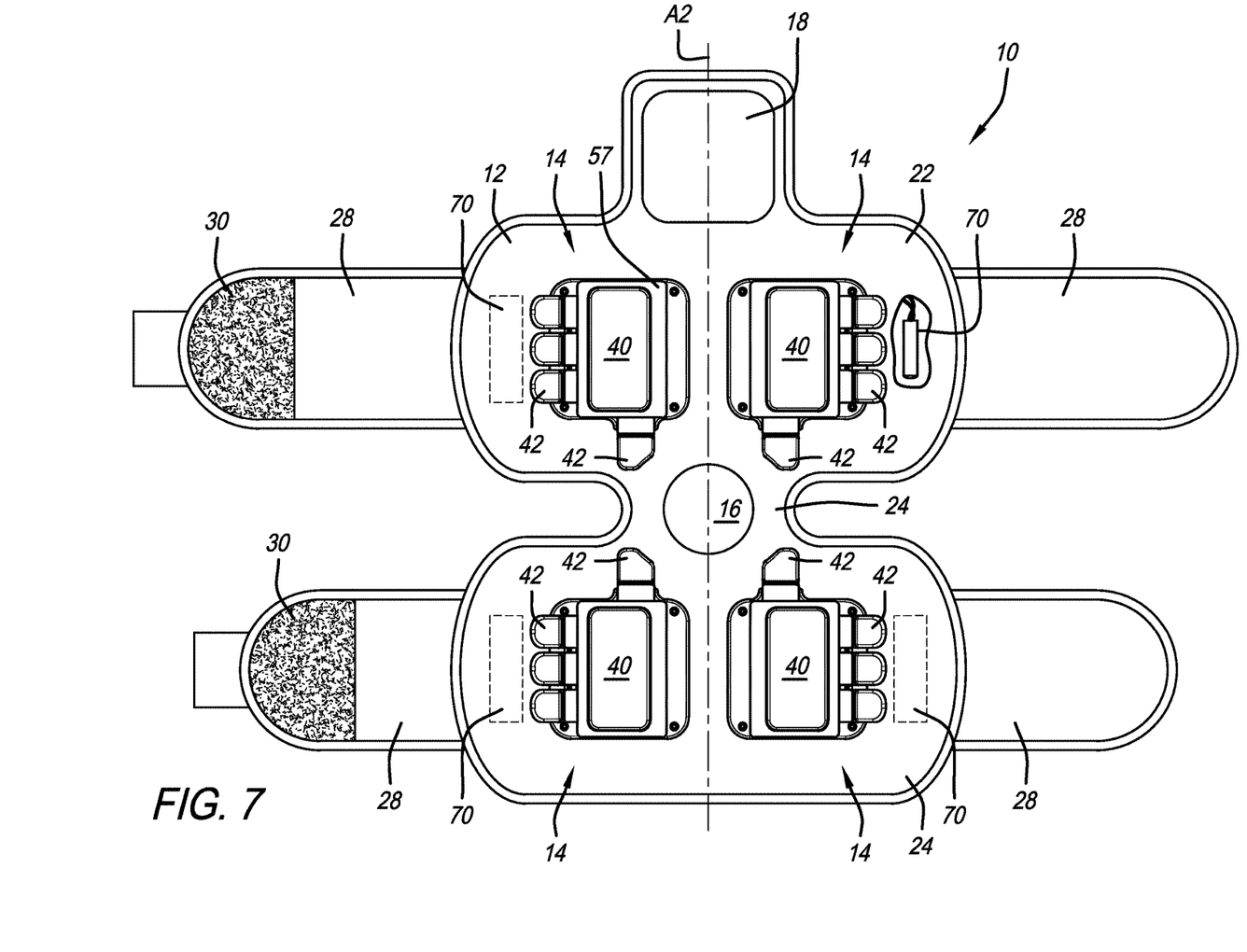
FIG. 7 is a rear elevational view of the temperature controllable wrap assembly of FIG. 1.

As shown in FIGS. 5 and 7, in a preferred embodiment, the temperature control module 14 includes a pad member 57 that at least partially covers the spreader member 40 and allows the contact portion 59 of the spreader member 42 to extend there around (see FIG. 7). The pad member 57 can be included to improve comfort. For example, it can be made of a soft material, such as TPE rubber or other rubber and overmolded onto the plastic lower portion of the housing.

It will be appreciated that in wrap assemblies for different portions of the body, different numbers of finger spreaders can be used in different places or extending from different sides of the main spreader member 40 in order to accommodate different portions, parts or shapes of the human anatomy. For example, as shown in FIG. 7, each of the temperature control modules 14 include three finger spreaders 42 extending outwardly therefrom and in a generally circumferential direction around the user's leg when the wrap assembly 10 is secured to a user's leg (they adapt to and are secured against the user's quadricep and calf) and one finger spreader 42 extending upwardly or downwardly toward the user's knee cap, such that they surround the knee cap when the wrap assembly is secured to the user's leg. The separate finger spreaders 42 provide flexibility to adapt to different sized user's body parts and geometries. When the wrap portion 12 is wrapped around the user's leg, the lower or inner surface of the wrap portion 12 contacts the upper surface of the finger spreader 42 and pivots the finger spreader 42 into contact with the user's skin.

As shown in FIG. 5, in a preferred embodiment, the wrap portion 12 is sandwiched between the upper portion 44 and the lower portion 46 of the housing 32. Preferably, the lower portion 46 includes a plurality of spike members 59 that engage the wrap portion 12 and help hold the temperature control module 14 on the wrap portion 12. As shown in FIG. 6, the lower portion 46 also includes rails 61 that contain the ends of the PCB 48. The lower portion 46 also includes knuckle portion recesses 63 in which the knuckle portions 50 of the spreader member 40 is received. Preferably, registration members 65 extend upwardly from the upper surface of the spreader member 40 and are received in registration openings 67 defined in the lower portion 46 of the housing 32.

Figure 8:
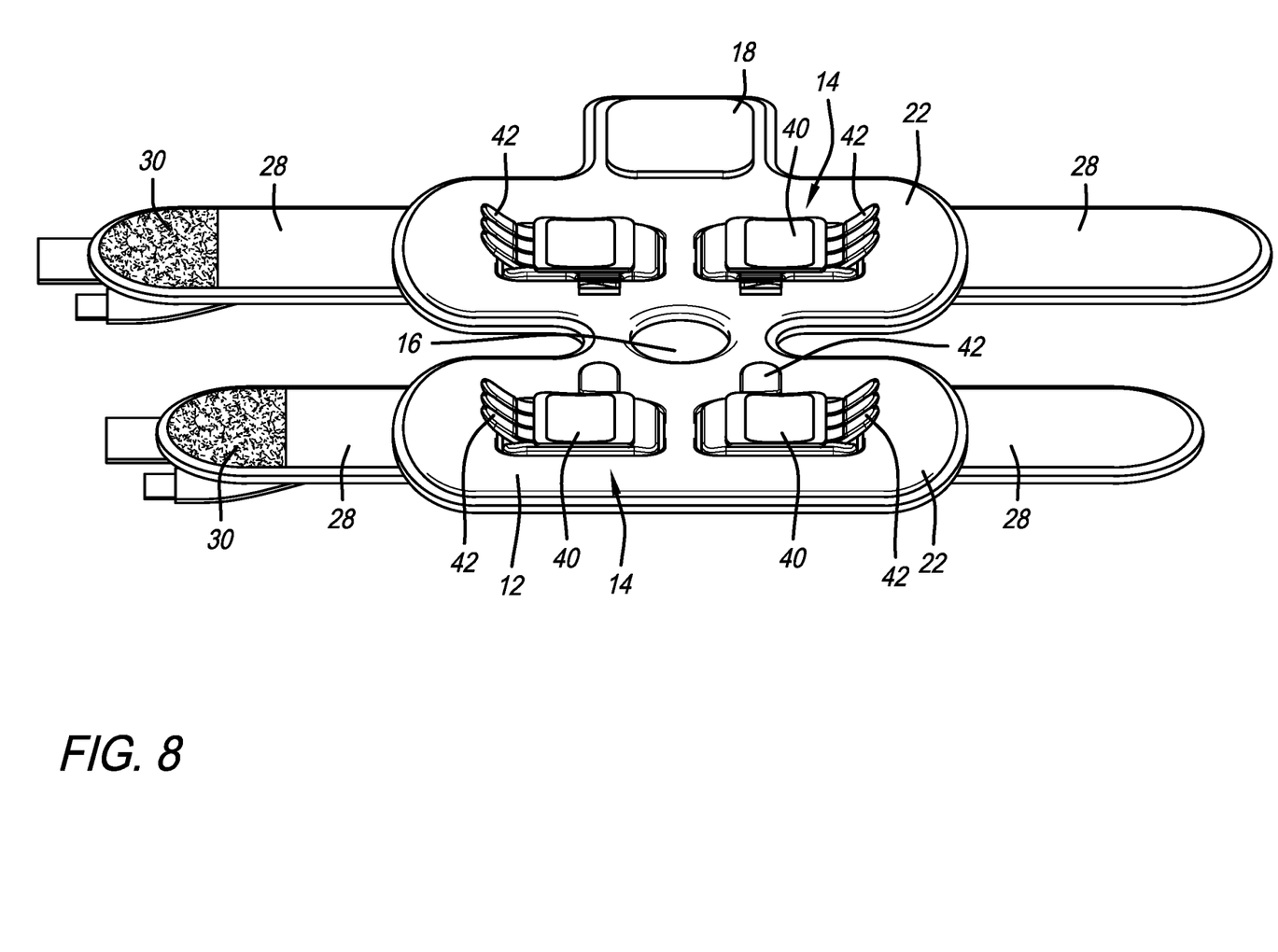
FIG. 8 is a rear perspective view of the temperature controllable wrap assembly of FIG. 1 in the open position.

As shown in FIGS. 7-8, the wrap assembly 10 includes temperature control modules 14 on opposite sides that include finger spreaders 42 extending outwardly in generally opposite directions (the three finger spreaders). It will be appreciated that because the finger spreaders are pivotable, they do not always extend or point in the same direction. Therefore, it should be understood by a person of ordinary skill in the art that, as shown in FIG. 7, three finger spreaders extend outwardly to the left and three finger spreaders extend outwardly to the right, but are not exactly 180° opposite to one another. And, anywhere within their range of pivotable motion, the three finger spreaders on the left still extend outwardly to the left and the three finger spreaders on the right still extend outwardly to the right. These arrangements meet the definition of generally outwardly and generally opposite from one another or in generally opposite directions. The finger spreaders 42 are each pivotable or movable along a pivot axis A1 (see FIG. 5) so that the bottom or contact surface of the finger spreader 42 is against the desired body part. It will be appreciated that in an embodiment with a plurality of finger spreaders 42, each of the finger spreaders 42 can individually be pivoted, moved or bent to provide further flexibility to make contact with a user's skin and to distribute the heat or cold.

As shown in FIGS. 7-8, in a preferred embodiment, the wrap assembly 10 also includes a plurality of vibration motors or devices 70 disposed in or on the wrap portion 12 and or the strap portions 28. FIGS. 7-8 show the vibration devices 70 in hidden lines, with one vibration device 70 in FIG. 7 exploded out therefrom to show an exemplary type of vibration device used therein. In a preferred embodiment, the vibration devices are located outside of the temperature control modules 14. In other words, the wrap portion 12 comprises a center axis A2 that extends between the temperature control modules 14 on either side. The temperature control modules 14 on the left are positioned between the vibration device(s) 70 on the left and the center axis and the temperature control modules 14 on the right are positioned between the vibration device(s) 70 on the right and the center axis.

Figure 10:
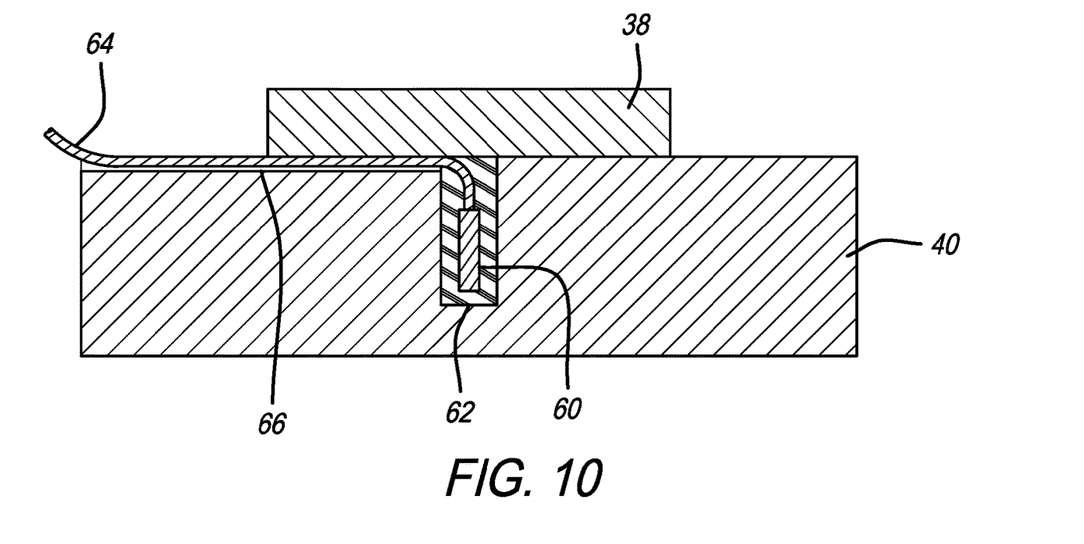
FIG. 10 is a cross-sectional view of the spreader member and thermistor.

As shown in FIGS. 9-10, in a preferred embodiment, a thermistor 60 or other temperature measurement device or sensor is positioned or embedded underneath the controllable temperature element 38 and preferably adjacent to the center of the controllable temperature element 38. FIG. 9 shows the thermistor 60 exploded from a thermistor opening 62 defined in the controllable temperature element 38. The thermistor 38 is in communication with the control system/main control module 18 (see wire 64, which extends through groove 66 defined in the upper surface of the spreader member 40) and contributes to the control of the temperature of the spreader member 40 and the temperature of the lower surface 40a that is against the user's skin. Positioning the thermistor 38 at or near the center of the spreader member 40 and/or controllable temperature element 38 allows monitoring of the hottest and coldest points at all times, thus increasing the accuracy of the control system and avoiding the spreader member 40 from becoming too hot or too cold and causing damage to the skin. FIG. 10 shows the thermistor 38 embedded in a material (epoxy, glue or other material) in thermistor opening 62.

As shown in FIGS. 1-3, the main control module 18 includes a plurality of buttons/switches 56 for controlling the wrap assembly 10. The main control module 18 is in electrical communication with the temperature control modules 14. In the exemplary embodiment shown in FIG. 1, the main control module 18 includes four buttons for controlling, from left to right, vibration, heat, cold and on/off. Shown below the vibration, heat and cold buttons are three LED lights for each. These represent different levels of vibration, heat and cold intensity when the buttons are pushed multiple times. In a preferred embodiment, the main control module 18 includes a removable battery module 58, as shown exploded outwardly in FIG. 3. Preferably, the battery module 58 can be pushed from one side (the opposite side in FIG. 3, as shown in FIG. 1) so that the battery module 144 slides out of the battery opening 58a defined in the main control module 18. The battery module 58 or main control module can include lights (e.g., LEDs) thereon that show the amount of charge remaining in the battery. In a preferred embodiment, the battery module 144 is magnetically secured within the battery opening 58a in the main control module and pushing the battery module with a predetermined amount of force overcomes the magnetic force so remove the battery module from the main control module.

In a preferred embodiment, the wrap assembly 10 includes a donut or ring member 72 positioned around the central opening 16. The ring member 16 may be embedded in the wrap portion 12 and preferably helps align the wrap assembly on the user's knee cap when worn.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description of the Preferred Embodiments using the singular or plural number may also include the plural or singular number respectively. The word "or" in reference to a list of two or more items, covers all of the following interpretations of the word: any of the items in the list, all of the items in the list, and any combination of the items in the list.

The above-detailed description of embodiments of the disclosure is not intended to be exhaustive or to limit the teachings to the precise form disclosed above. While specific embodiments of and examples for the disclosure are described above for illustrative purposes, various equivalent modifications are possible within the scope of the disclosure, as those skilled in the relevant art will recognize. Further, any specific numbers noted herein are only examples: alternative implementations may employ differing values, measurements or ranges.

Although the operations of any method(s) disclosed or described herein either explicitly or implicitly are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

The teachings of the disclosure provided herein can be applied to other systems, not necessarily the system described above. The elements and acts of the various embodiments described above can be combined to provide further embodiments. Any measurements or dimensions described or used herein are merely exemplary and not a limitation on the present invention. Other measurements or dimensions are within the scope of the invention.

Any patents and applications and other references noted above, including any that may be listed in accompanying filing papers, are incorporated herein by reference in their entirety. Aspects of the disclosure can be modified, if necessary, to employ the systems, functions, and concepts of the various references described above to provide yet further embodiments of the disclosure.

These and other changes can be made to the disclosure in light of the above Detailed Description of the Preferred Embodiments. While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features or aspects of the disclosure with which that terminology is associated. In general, the terms used in the following claims should not be construed to limit the disclosures to the specific embodiments disclosed in the specification unless the above Detailed Description of the Preferred Embodiments section explicitly defines such terms. Accordingly, the actual scope of the disclosure encompasses not only the disclosed embodiments, but also all equivalent ways of practicing or implementing the disclosure under the claims.

While certain aspects of the disclosure are presented below in certain claim forms, the inventors contemplate the various aspects of the disclosure in any number of claim forms. For example, while only one aspect of the disclosure is recited as a means-plus-function claim under 35 U.S.C. § 112, ¶6, other aspects may likewise be embodied as a means-plus-function claim, or in other forms, such as being embodied in a computer-readable medium. (Any claims intended to be treated under 35 U.S.C. § 112, ¶6 will include the words "means for"). Accordingly, the applicant reserves the right to add additional claims after filing the application to pursue such additional claim forms for other aspects of the disclosure.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A temperature controllable wrap assembly comprising:
   a wrap portion configured to be worn around a user's body part;
   a first temperature control module positioned on the wrap portion, wherein the first temperature control module includes:
   a housing;
   a controllable temperature element;
   a spreader member; and
   a first finger spreader pivotably attached to the spreader member, wherein a lower surface of the spreader member is positioned to contact the user's body part, wherein the controllable temperature element is configured to transfer thermal energy to an upper surface of the spreader member, and wherein the spreader member is configured to conduct the thermal energy to the first finger spreader; and
   a main control module in electrical communication with the first temperature control module, wherein the main control module includes a removable battery, wherein the main control module includes an upper battery opening defined in an upper surface of the main control module and a lower battery opening defined in a lower surface of the main control module, wherein the removable battery includes a lower battery surface that is exposed through the lower battery opening and an upper battery surface that is exposed through the upper battery opening, and wherein the removable battery is removable by pushing on the lower battery surface and removing the removable battery through the upper surface of the main control module.

2. The temperature controllable wrap assembly of claim 1, wherein the lower surface of the spreader member is curved.

3. The temperature controllable wrap assembly of claim 1, wherein the first finger spreader is pivotable between a first position and a second position, wherein in the second position a distal end of the first finger spreader is positioned below the lower surface of the spreader member.

4. The temperature controllable wrap assembly of claim 3, wherein the spreader member includes a knuckle portion, wherein the first finger spreader includes a pin portion that is received in the knuckle portion, and wherein the pin portion is rotatable within the knuckle portion.

5. The temperature controllable wrap assembly of claim 1, wherein the removable battery includes a magnet for holding the removable battery within the main control module.

6. The temperature controllable wrap assembly of claim 1, further comprising:
   a second temperature control module positioned on the wrap portion, wherein the second temperature control module includes:
   a housing;
   a controllable temperature element;
   a spreader member; and
   a second finger spreader pivotably attached to the spreader member of the second temperature control module, wherein a lower surface of the spreader member of the second temperature control module is positioned to contact the user's body part, wherein the controllable temperature element of the second temperature control module is configured to transfer thermal energy to an upper surface of the spreader member of the second temperature control module, wherein the spreader member of the second temperature control module is configured to conduct the thermal energy to the second finger spreader, wherein the first finger spreader extends outwardly in a first direction, and wherein the second finger spreader extends outwardly in a second direction, and wherein the first direction is generally opposite of the second direction.

7. The temperature controllable wrap assembly of claim 6, further comprising a vibration device embedded in the wrap portion.

8. The temperature controllable wrap assembly of claim 6, further comprising first and second vibration devices embedded in the wrap portion, wherein the wrap portion comprises a center axis that extends between the first and second temperature control modules, wherein the first temperature control module is positioned between the first vibration device and the center axis and the second temperature control module is positioned between the second vibration device and the center axis.

9. The temperature controllable wrap assembly of claim 1, wherein a thermistor is embedded in the spreader member.

10. The temperature controllable wrap assembly of claim 9, wherein the thermistor is received in a thermistor opening defined in the upper surface of the spreader member, wherein a groove is defined in the upper surface of the spreader member, and wherein a wire extends from the thermistor and through the groove.

11. A temperature control module comprising:
a housing;
a controllable temperature element having a first surface and a second surface, wherein the first surface opposes the second surface;
a heat sink positioned in the housing and in contact with the first surface of the controllable temperature element;
a fan positioned in the housing and configured to direct heat away from the heat sink;
a spreader member, wherein the controllable temperature element is configured to transfer thermal energy to an upper surface of the spreader member;
a first finger spreader pivotably attached to the spreader member, wherein the spreader member is configured to conduct thermal energy to the first finger spreader; and
a second finger spreader, wherein the first and second finger spreaders are pivotable with respect to the housing and independently from one another,
wherein the spreader member includes first and second opposing edges and third and fourth opposing edges, wherein the first finger spreader extends outwardly past the first opposing edge and the second finger spreader extends outwardly past the third opposing edge such that the first and second finger spreaders are perpendicular to one another.

12. The temperature control module of claim 11, wherein a lower surface of the spreader member is curved.

13. The temperature control module of claim 11, wherein the first finger spreader is pivotable between a first position and a second position, wherein in the second position a distal end of the first finger spreader is positioned below a lower surface of the spreader member.

14. The temperature control module of claim 13, wherein the spreader member includes a knuckle portion, wherein the first finger spreader includes a pin portion that is received in the knuckle portion, and wherein the pin portion is rotatable within the knuckle portion.

15. The temperature control module of claim 11, wherein a thermistor is embedded in the spreader member.

16. The temperature control module of claim 15, wherein the thermistor is received in a thermistor opening defined in the upper surface of the spreader member, wherein a groove is defined in the upper surface of the spreader member, and wherein a wire extends from the thermistor and through the groove.

17. A temperature control module comprising:
a housing;
a controllable temperature element having a first surface and a second surface, wherein the first surface opposes the second surface;
a heat sink positioned in the housing and in contact with the first surface of the controllable temperature element;
a fan positioned in the housing and configured to direct heat away from the heat sink;
a spreader member, wherein the controllable temperature element is configured to transfer thermal energy to an upper surface of the spreader member, wherein a lower surface of the spreader member is curved; and
first and second finger spreaders pivotably attached to the spreader member, wherein the spreader member is configured to conduct thermal energy to the first and second finger spreaders, wherein the first and second finger spreaders are pivotable independently between a first position and a second position, wherein, in the second position, distal ends of the first and second finger spreaders are positioned below the lower surface of the spreader member, wherein the spreader member includes first and second opposing edges and third and fourth opposing edges, wherein the first finger spreader extends outwardly past the first opposing edge and the second finger spreader extends outwardly past the third opposing edge such that the first and second finger spreaders are perpendicular to one another, wherein the spreader member includes a knuckle portion, wherein the first finger spreader includes a pin portion that is received in the knuckle portion, and wherein the pin portion is rotatable within the knuckle portion.

18. The temperature control module of claim 17, wherein a thermistor is embedded in the spreader member.

19. The temperature control module of claim 17, wherein the controllable temperature element is a thermoelectric cooler.

20. The temperature control module of claim 17, positioned on a wrap portion configured to be worn around a user's body part.

* * * * *